(12) United States Patent
Ghobrial et al.

(10) Patent No.: US 8,740,954 B2
(45) Date of Patent: Jun. 3, 2014

(54) DEVICE AND METHOD FOR ORTHOPEDIC FRACTURE FIXATION

(75) Inventors: Eman K. R. Ghobrial, San Diego, CA (US); Bassem Georgy, San Diego, CA (US)

(73) Assignee: Integral Spine Solutions, Inc., Carlsbad, CA (US)

( * ) Notice: Subject to any disclaimer, the term of this patent is extended or adjusted under 35 U.S.C. 154(b) by 620 days.

(21) Appl. No.: 12/339,009

(22) Filed: Dec. 18, 2008

(65) Prior Publication Data
US 2009/0164016 A1    Jun. 25, 2009

Related U.S. Application Data

(60) Provisional application No. 61/014,748, filed on Dec. 19, 2007.

(51) Int. Cl.
*A61B 17/04* (2006.01)
*A61B 17/86* (2006.01)
*A61F 2/08* (2006.01)

(52) U.S. Cl.
USPC ........... 606/310; 606/313; 606/318; 606/327; 606/92

(58) Field of Classification Search
USPC ........ 604/264–279; 606/60–63, 300–331, 68, 606/92–95
See application file for complete search history.

(56) References Cited

U.S. PATENT DOCUMENTS

| 4,466,435 A * | 8/1984 | Murray ........................ 606/94 |
|---|---|---|
| 4,653,489 A | 3/1987 | Tronzo |
| 4,959,058 A | 9/1990 | Michelson |
| 6,019,776 A | 2/2000 | Preissman et al. |
| 6,033,411 A | 3/2000 | Preissman |
| 6,214,012 B1 | 4/2001 | Karpman et al. |
| 6,676,663 B2 | 1/2004 | Higueras et al. |
| 7,008,433 B2 | 3/2006 | Voellmicke et al. |
| 7,255,713 B2 | 8/2007 | Malek |
| 2003/0074075 A1 | 4/2003 | Thomas, Jr. et al. |
| 2003/0171812 A1 | 9/2003 | Grunberg et al. |
| 2004/0059328 A1* | 3/2004 | Daniel et al. ................... 606/41 |
| 2005/0015059 A1* | 1/2005 | Sweeney ...................... 604/264 |
| 2006/0074433 A1 | 4/2006 | McGill et al. |
| 2007/0083205 A1* | 4/2007 | Attawia et al. .................. 606/72 |

OTHER PUBLICATIONS

Hierholzer et al. J. Vasc. Interv. Radiol. 2003; 14:773-777.
Heini, Spine, vol. 27. No. 1, pp. 105-109, 2002.

* cited by examiner

*Primary Examiner* — Andrew Yang
*Assistant Examiner* — Olivia C Chang
(74) *Attorney, Agent, or Firm* — Gary L. Loomis; G.L. Loomis & Associates, Inc.

(57) ABSTRACT

The present invention relates invention relates to devices and methods for the fixation and stabilization of orthopedic fractures and more specifically to stabilization of compression fractures of spinal vertebrae. The systems comprise cannulated orthopedic screws and mechanical expandable implants introducible through the lumen of such screws. In certain embodiments the cannulated implants are expandable within an intraosseous space to introduce scaffold-like structures such that subsequent introduction of a bone cement forms a composite in situ. The devices and methods are also particularly useful for stabilizing the orthopedic screws.

13 Claims, 6 Drawing Sheets

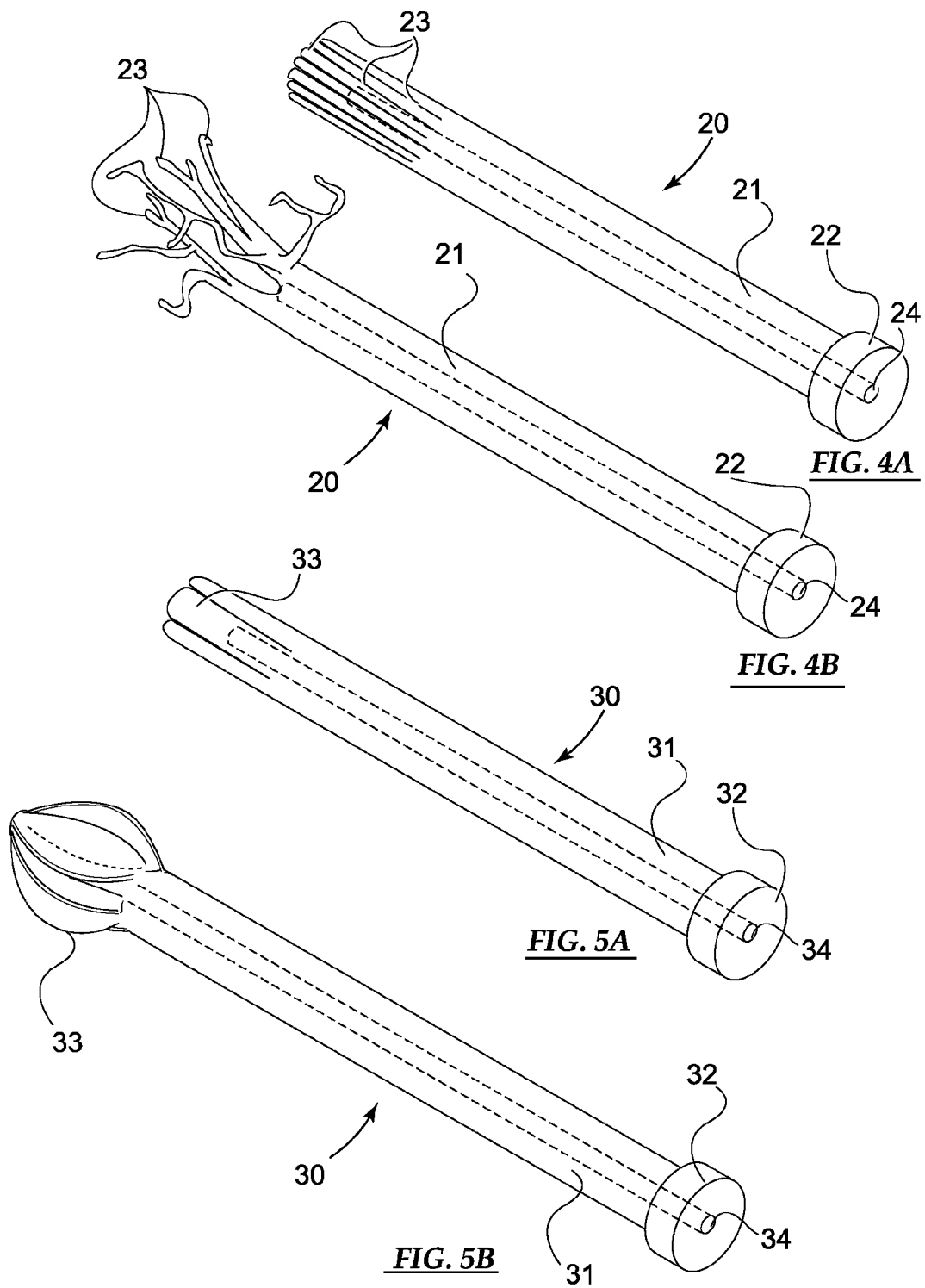

DEVICE AND METHOD FOR ORTHOPEDIC FRACTURE FIXATION

RELATED APPLICATION DATA

This application claims priority under 35 U.S.C. §119(e) to U.S. Provisional Application Ser. No. 61/014,748, filed Dec. 19, 2007.

FIELD OF THE INVENTION

This invention relates to devices and methods for the fixation and stabilization of orthopedic fractures. More specifically, these devices and methods apply to stabilization of compression fractures of spinal vertebrae.

BACKGROUND

The mammalian spine consists of bones called vertebrae, which are separated by soft cushions referred to as intervertebral discs. The thick portion of bone at the front of each vertebra is referred to as the vertebral body. When a vertebral body collapses, a vertebral compression fracture (VCF) of the bone results. Most vertebral compression fractures are caused by osteoporosis, a disease that causes bones to become brittle and to break easily. Because osteoporosis usually progresses without obvious symptoms, an individual may not be aware that he or she has the disease until a fracture actually occurs. The pain and loss of movement that often accompanies fractures of the spine are perhaps the most feared and debilitating side effects of osteoporosis. When a spinal compression fracture occurs as a result of osteoporosis, the vertebrae in the thoracic (chest) and lower spine that are usually affected. For many people with osteoporosis a spinal fracture results in severely limited activity, constant pain and serious reduction in quality of life.

While there is no known cure for osteoporosis, there are treatments and prevention measures available to reduce the risk of pathologic fractures. The three mainstays of osteoporosis treatment are (1) weight-bearing exercise; (2) nutrition supplementation such as supplemental calcium; and (3) medications such as bisphosphonates, calcitonin, raloxifene and estrogen. Despite such treatments approximately 700,000 vertebral compression fractures occur each year, usually in women over the age of 60, and it has been estimated that at least 25 percent of women and a somewhat smaller percentage of men over the age of 50 will suffer one or more spinal fractures.

Other medical conditions known to contribute to vertebral compression fractures include cancer, benign tumors or lesions and various types of trauma. Cancerous lesions include multiple myeloma and metastatic lesions, including those arising from breast or lung cancer, or lymphoma, while benign lesions include hemangioma and giant cell tumors. Additionally, younger individuals may also suffer such vertebral compression fractures, particularly individuals whose bones have become fragile due to the long-term use of steroids or other drugs to treat a variety of diseases such as lupus, asthma and rheumatoid arthritis.

Various treatments are currently available for spinal compression fractures and such fractures may also be treated symptomatically with pain medicines. While various types of back bracing devices can also be used, such devices may actually cause weakening of the bone and predispose patients to further fractures in the future. If a compression fracture is caused by trauma, a rigid bracing that protects the bone as it heals may be required for six to ten weeks.

Many cases of vertebral compression fractures require surgery. When the compression fracture is caused by a tumor, a biopsy procedure may be performed followed by treatment of the tumor. A surgical procedure may also be required to remove any bone within the spinal canal, followed by the fusing together of the vertebra in order to stabilize the spine. Surgery is almost always required whenever there is a loss of function caused by the impingement of bone on the spinal cord or spinal nerves.

Recently, minimally invasive techniques, such as percutaneous vertebroplasty, have been used to treat compression fractures. Vertebroplasty is an image-guided, minimally invasive, non-surgical procedure used to strengthen a fractured spinal vertebra. Often performed on an outpatient basis, such procedures are normally carried out with the patient immobilized lying face down on his or her stomach while under local anesthesia and light sedation and intravenous antibiotics may also be administered to prevent infection. Then, through a small incision and under the guidance of a special x-ray imaging technique a cannulated bone needle designed for intraosseous access is guided through the skin and passed through the spinal muscles until the needle tip is precisely positioned within the fractured vertebra. At this point the interventional radiologist may perform an examination called intraosseous venography to insure that the bone needle has resides in the desired area within the fractured bone. Finally, biocompatible liquid orthopedic cement is injected through the bone needle to fill the vertebral cavity and as the needle is withdrawn, the cement hardens thereby stabilizing the vertebra and thus preventing further vertebral body collapse.

Although successful vertebroplasty has been shown to alleviate the pain caused by a compression fracture, these techniques are often deficient providing adequate stability and physiologic reconstruction of the spinal column and often prevents patients from return to a previous level of physical activity.

In vertebroplasty the most commonly used bone cements are curable compositions of poly(methyl methacrylate) containing radiopacifiers such as barium powder that render the cement visible by the same imaging technique used to guide the bone needle. It is evident that as the technology matures and become more sophisticated, there is a need for better visualization techniques to perform such complicated and delicate procedures since X-ray (fluoroscopic) guidance is the only available modality for visualization during the performance of vertebroplasty to date. Although a variety of direct visualization techniques including optical visualization (endoscopes), ultrasonography, and laser beams are well known in the art, to date these techniques have been used only in body cavities other than bony tissue.

Another minimally invasive treatment for spinal compression fractures is the balloon-assisted vertebroplasty technique known as balloon kyphoplasty. In a kyphoplasty procedure, as in a percutaneous vertebroplasty procedure, a cement-like material is injected directly into the fractured bone, however kyphoplasty includes an additional step the goal of which is to restore height to the bone thus reducing deformity of the spine. In a balloon kyphoplasty procedure an inflatable orthopedic balloon is inserted between the pieces of a collapsed vertebra and the balloon is carefully inflated to gently raise the collapsed vertebra and return it to a more normal position while the inner soft bone is compacted to create a cavity inside the vertebral body. The balloon is then deflated and removed and pasty orthopedic cement is injected through a bone needle to fill the vertebral cavity wherein the cement hardens to stabilize the raised vertebra and prevent further vertebral body collapse. However, as in the vertebroplasty procedures, balloon kyphoplasty techniques are often insufficient in providing adequate stability and physiologic reconstruction of the spinal column and often prevents patients from return to a previous level of physical activity.

Whereas the percutaneous vertebroplasty procedures discussed above are well described and widely accepted, osteoplasty of bones outside the spine is less known but is being actively studied. For example, a clinical study published by Hierholzer et al. in Journal of Vascular and Interventional Radiology, vol. 14, pp. 773-778 (2003) describes patients with painful metastases to the pelvis, ilium, or femur who were successfully treated by injection of acrylic cement into the osteolytic defect under fluoroscopic or computed tomographic (CT) guidance. Therefore, it is expected that percutaneous osteoplasty of bones outside the spine will become widely accepted.

Devices for delivering injectable biomaterials such as bone cement formulations into body cavities are known in the art. U.S. Pat. No. 7,008,433 to Voellmicke et al. describes a high-pressure bone cement injection device for use in vertebroplasty that allows for specific control of the injection of small discrete quantities of the cement. Published U.S. Pat. Application No. 2006/0074433 to McGill et al. describes an apparatus for delivering bone cement into a vertebra that includes a cannula and a pressurized delivery device in communication with the cannula. This pressurized delivery device provides an actuating force that acts either directly or through a medium to cause a flowable compound to be delivered from the delivery device to the cannula and into the vertebra. While the above referenced devices address problems relating to the viscosity of flowable compositions such as bone cements, they do not address issues relating to the precise control of placement and distribution of such compositions at a targeted injection site.

U.S. Pat. Nos. 6,019,776 and 6,033,411 to Preissman, et al. disclose methods for a controlled approach to the interior of a vertebral body involving insertion of a threaded or sharp-pointed stylet and cannula percutaneously through the soft tissue of a patient until hard tissue is abutted; further insertion of the stylet to a predetermined site within the hard tissue; ratcheting a pawl mechanism or rotating a camming mechanism to advance the cannula along the stylet to the predetermined site; withdrawing the stylet from the cannula and attaching a source of implantable material for injection of the material into the site through the cannula. U.S. Pat. No. 6,676,663 to Higueras et al. describes an applicator device utilizing a standard syringe body for controllably injecting a quantity of cement into bones, particularly, in percutaneous vertebroplasty. However, the devices described in these patents deliver the injected material only through the tip of cannula and therefore offer no control of the direction or distribution of the injected material within the organism. Furthermore, these patents do not teach methods for delivery of restorative material by percutaneous vertebroplasty by which multiple doses of material can be injected.

A report by Heini et al. in SPINE, vol. 27, No. 1, pp. 105-109 (2002) describes the evaluation of an injection cannula for the delivery of bone cement in vertebroplasty procedures using human cadaver bones, wherein the injection cannula has a single opening in the cannula wall through which the bone cement is dispensed. These researchers indicate that use of a side-opening cannula may reduce the likelihood of cement leakage into adjacent veins and subsequent embolization. However, such a cannula with a single opening in the cannula wall as described does not provide sufficient control of cement placement nor degree of directional control required to prevent extravasation in these delicate procedures.

U.S. Pat. No. 4,959,058 to Michelson describes a cannula for use with an arthroscope wherein the cannula has multiple openings in the form of multiple narrow slots radially disposed about the tip. These openings are designed to allow a low viscosity fluid such as water to be injected in a shower-like fashion as a viewing aid during the arthroscopic procedure. Such a cannula is not suitable for the injection of viscous flowable materials such as bone cement and, since the narrow openings are confined near the tip of the cannula, such a design offers no control over the placement of the fluid.

Bone screws for spinal compression fractures are well know in the art. Furthermore, U.S. Pat. No. 7,255,713 to Malek describes cannulated bone screws for delivering a treatment agent to a bone or a prosthetic vertebral body. U.S. Pat. No. 6,214,012 to Kartman et al. also describes a cannulated bone screw, which is configured for delivery of an injectable material into a bone. U.S. Pat. No. 4,653,489 to Tronzo et al. describes a fenestrated cannulated hip screw adapted for introduction of bone cement into a bone region for increase of overall fixation of hip fractures.

Various mechanical devices for the fixation and stabilization of various orthopedic fractures are know in the art. For example, US Patent Application 2003/0171812 to Grunberg et al. describes a modular support implant device consisting of a plurality of rigid plates for reconstructing and supporting a diseased or fractured bone or within a space previously occupied by a diseased intervertebral dis. The individual plates are sized to be inserted into the bone or the space through a cannula and are arranged in situ relative the adjacent plates to construct a scaffold that to function as a supporting prosthesis. US Patent Application 2003/0074075 to James et al. describes expandable implants for orthopedic uses wherein the implants are inserted into an annular defect by forceps or forcep-like implantation devices.

Therefore, in view of the prior art, there exists a need for devices and methods that permit effective delivery of a mechanical implant such as a scaffold into a bone cavity with concurrent or sequential delivery of a flowable material such as bone cement and wherein the mechanical implant is secured by an anchoring means.

There also exists a need for devices and methods for the securing the bone screws used in orthopedic procedures such as fracture fixation.

There exists a need for a reliable integrated system for fracture fixation and other such procedures that integrates the delivery of mechanical implants and introduction of bone cement wherein the system also functions to secure bone screws used in the procedure.

There exist yet other needs to provide minimally invasive techniques for the reparation and restoration of bony structures and to provide minimally invasive techniques for the augmentation of procedures requiring screw fixation.

The devices and methods of the present invention address these and other needs that will become apparent to those skilled in the art based on the following specification and the accompanying drawings.

SUMMARY OF THE INVENTION

The present invention provides a reliable integrated system for fracture fixation and other such procedures wherein the delivery of mechanical implants and introduction of flowable compositions such as bone cement into an intraosseous space are integrated. The devices and methods are useful anywhere in the axial or peripheral skeleton of a mammalian body. The systems comprise cannulated orthopedic screws and mechanical expandable implants introducible through the lumen of such screws wherein the system is configured such that the expandable proximal end of the implant remains attached to the cannulated screw to provide an anchor for the implant. In preferred embodiments the cannulated implants are expandable within the intraosseous space to introduce a scaffold-like structure such as branched, basket, mesh umbrella and the like and wherein after subsequent introduction of a flowable composition such as bone cement the device functions to secure the bone screw and prevents the subsequent post-operative loosening of bone screws often observed months or years after the fixation procedure. The devices are also particularly useful for delivering flowable restorative compositions into an osseous cavity.

A typical embodiment of an orthopedic fracture fixation device of the present invention comprises a cannulated orthopedic screw comprising a through-bore along the longitudinal axis that defines an orthopedic screw lumen extending between an open orthopedic screw proximal end and an open orthopedic screw distal end; a screw cap attachable to the orthopedic screw proximal end that functions to seal the orthopedic screw proximal end; and a cannulated implant sized and configured to be slidably disposable within the through-bore of the orthopedic screw wherein the cannulated implant distal end comprises an expandable region that is disposed beyond the orthopedic screw distal end when the cannulated implant proximal end is disposed completely within the orthopedic screw through-bore and wherein the expandable region of the cannulated implant is expanded to assume a predetermined configuration when disposed within a targeted location in a mammalian body. The combination of the implanted structure and the bone cement stabilize the fractured bone.

This devices of the present invention are useful for treatment and stabilization of malignant or traumatic vertebral compression fracture of the spine and the combination of the nitinol implanted structure and the bone cement stabilizes and reconstructs the affected vertebra.

Certain embodiments of the present invention employ cannulated screws with side ports or holes wherein a pre-shaped expandable implant in a compressed state is inserted inside the cannulated screw and branch-like elements of the implant situated along the shaft of the implant are extend outside of the screw through the sides ports for additional stabilization. Such devices are particularly useful in spinal procedures or in treatment of fractures of long bones like tibia wherein it is desirable to prevent loosening of the screws.

Also in accordance with the present invention, there are provided devices and methods for dispensing flowable compositions into cavities that exist in or that can be formed or created in bones. More particularly the invention provides devices and methods for injecting a flowable composition such as bone cement into an interior region of a vertebral body.

BRIEF DESCRIPTION OF THE DRAWINGS

FIG. 4A depicts an isometric view of an expandable cannulated implant having a branched distal end configuration in a compressed state.

FIG. 4B depicts an isometric view of an expandable cannulated implant having a branched distal end configuration in an expanded state.

FIG. 5A depicts an isometric view of an expandable cannulated implant having a basket-like distal end configuration in a compressed state.

FIG. 5B depicts an isometric view of an expandable cannulated implant having a basket-like distal end configuration in an expanded state.

Figure 1:
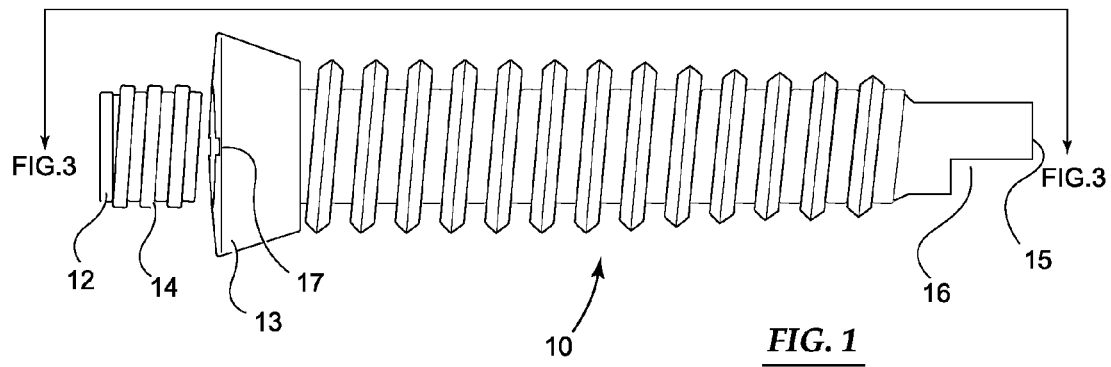
FIG. 1 depicts a frontal orthographic view of an embodiment of a cannulated bone screw provided with a sealing cap.

Although the figures illustrate some preferred embodiments, they are intended to be merely exemplary and representative of certain embodiments. To that end, several figures contain optional features that need not be included in any particular embodiment of the invention. Furthermore, the shapes, types, or particular configurations of the various elements of the illustrated devices should not be regarded as limiting to the invention.

DETAILED DESCRIPTION OF THE INVENTION

For the purposes of the invention described in this application, the certain terms shall be interpreted as shown below.

The term 'cannulated' describes the property of an object as being hollow or tubular and affording a passage through its interior length for a flowable materials and suitably sized solid objects such as catheters, rods, wires, threads, and the like.

The term 'side-port' describes any orifice in the wall of a tube, pipe or cannula that allows communication between the lumen of the tube, pipe or cannula and an outside area.

The term 'flowable material' describes any injectable material that flows as a uniform mass when an appropriate pressure is applied. Such flowable materials may comprise solutions, emulsions, suspensions, slurries, pastes, gels, polymerizable monomers, liquid polymers, oligomers, and all mixtures or combinations thereof.

Basic embodiments of the orthopedic fixation devices of the present invention comprise: a cannulated orthopedic bone screw with a through-bore defining a cannulated screw lumen along the longitudinal axis extending between open proximal and distal ends; a screw cap attachable to the orthopedic screw proximal end that functions to seal the orthopedic bone screw proximal end; and a cannulated implant sized and configured to be slidably disposable within the through-bore of the orthopedic screw wherein the cannulated implant distal end comprises an expandable region that is disposed beyond the bone screw distal end when the cannulated implant proximal end is disposed completely within the cannulated bone screw through-bore and wherein the expandable region of the cannulated implant can be expanded to assume a predetermined configuration when disposed within a targeted location in a mammalian body. In a typical procedure the cannulated screw is inserted into a desired location in a mammalian skeleton followed by insertion of the cannulated expandable implant. After expansion of the implant a flowable composition such as bone cement is introduced through the implant cannula and a screw cap is affixed to the proximal end of the orthopedic screw to effect a seal.

In certain orthopedic procedures cannulated screw is introduced into a desired site such as a vertebral pedicle over a Kirschner wire, which is also known as a K wire.

An example of a method for fracture fixation of a spinal vertebra utilizing the devices of the present invention comprises the steps of installing a cannulated orthopedic screw through a vertebral wall such that distal portion of the orthopedic screw extends into a vertebral cavity; slidably inserting the cannulated implant within the through-bore of the orthopedic screw such that the expandable region of the cannulated implant is disposed beyond the cannulated orthopedic screw distal end wherein the expandable region of the cannulated implant is caused or allowed to expand; dispensing a flowable composition such as bone cement though the cannulated implant into the vertebral cavity; and affixing the screw cap to the orthopedic screw proximal end to effect a seal.

Figure 2:
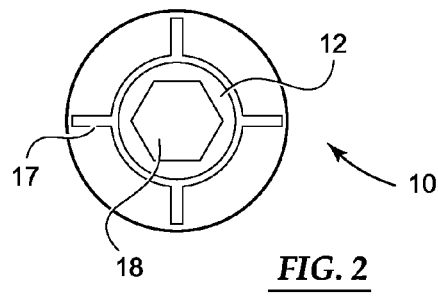
FIG. 2 depicts an end orthographic view of an embodiment of a cannulated bone screw provided with a sealing cap.
Figure 3:
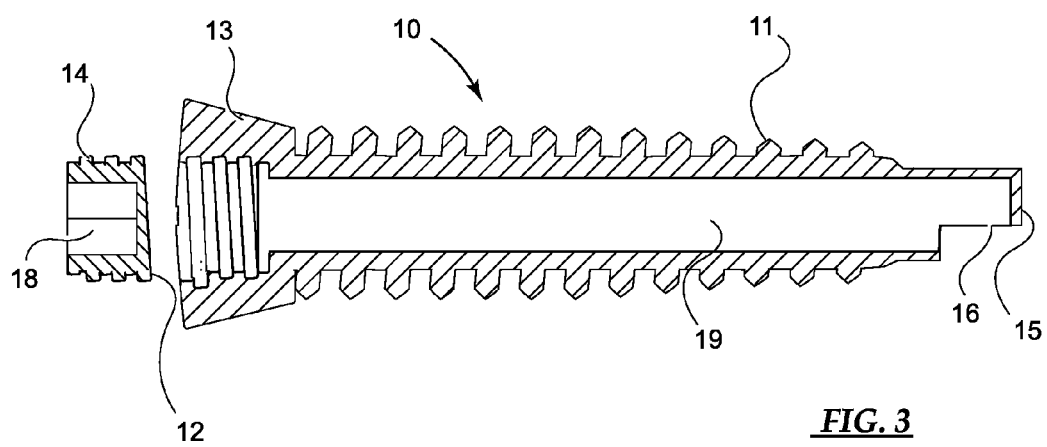
FIG. 3 depicts a sectional frontal orthographic view of the embodiment of the cannulated bone screw provided with a sealing cap depicted in FIG. 1.

In FIG. 1 is depicted a frontal orthographic view of an embodiment of a cannulated bone screw component 10 and a sealing screw cap of the present invention wherein a cannulated bone screw 11 is provided with sealing cap 12 having external threads 14 that mate to internal threads within the bone screw head 13. The cannulated bone screw 11 has a closed distal end 15 and a single side port opening 16 disposed at the distal tip. In FIG. 2 is depicted an end orthographic view of the embodiment of the cannulated bone screw component 10 depicted in FIG. 1 having the sealing screw cap 12 affixed. In this embodiments the bone screw head 13 is provide with four perpendicular slots 17 to accommodate a single slot screw driver tool or a Phillips head screw driver tool, while the sealing cap 12 is provided with an internal hexagonal configuration 18 to accommodate an allen wrench type tool. However such tool accommodating configurations are intended to be merely exemplary and representative of certain embodiments illustrated devices should not be regarded as limiting to the invention and any standard configuration/tool combination can be utilized. In FIG. 3 is depicted a sectional frontal orthographic view of the embodiment of the cannulated bone screw 10 depicted in FIG. 1, which clearly illustrates the lumen 19 extending completely through the bone screw body 11 from the proximal screw head 13 to the port opening 16 at the tip of the closed distal end 15. A port opening such as port opening 16 is a configuration useful for effecting a desired placement of the expanded implant. However, those with skill in the art will recognized that such a bone screw distal tip configuration for controlling placement of the expanded implant is not limiting and that many other configurations can be utilized depending upon the size and geometry of the implant and the implant site.

In FIG. 4A is depicted an embodiment of a cannulated implant 20 clearly showing the through-bore 24 extending through implant shaft 21. The proximal end of the implant 20 has a flange 22 the diameter of which is sized to fit into the head portion of the mating cannulated bone screw but less than the diameter of the shaft portion of the mating cannulated bone screw so that the expandable implant 20 is coupled to the bone screw when the expandable portion 23 of the implant 20 is disposed within an osseous cavity. The expandable portion of the distal end of the implant 20 has multiple branches 23 which are shown in FIG. 4A in a compressed state. FIG. 4B depicts implant 20 wherein the multiple branches 23 are in an expanded state.

In FIG. 5A is depicted an embodiment of a cannulated implant 30 clearly showing the through-bore 34 extending through implant shaft 31. The proximal end of the implant 30 has a flange 32 the diameter of which is sized to fit into the head portion of the mating cannulated bone screw but less than the diameter of the shaft portion of the mating cannulated bone screw so that the expandable implant 30 is coupled to the bone screw when the expandable portion 33 of the implant 30 is disposed within an osseous cavity. The expandable portion of the distal end of the implant 30 has a cage-like configuration 33, which is shown in FIG. 5A in a compressed state. FIG. 5B depicts implant 30 wherein the cage-like configuration 33 is expanded.

Figure 6:
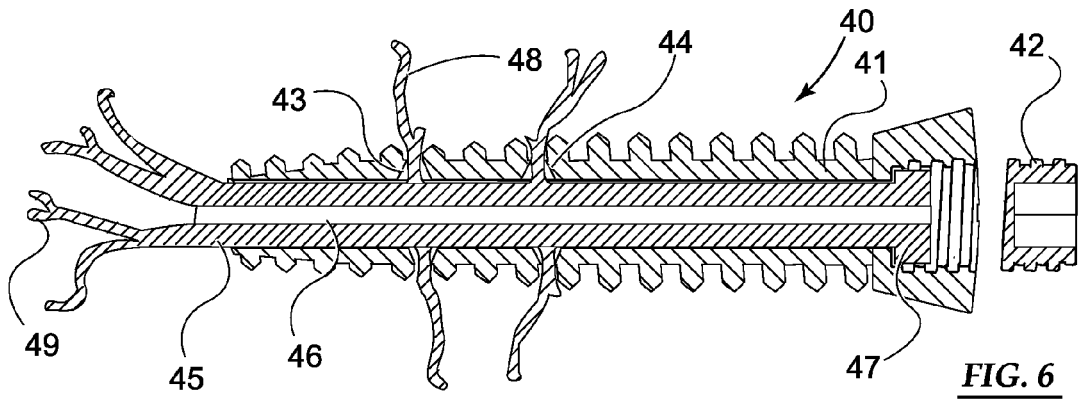
FIG. 6 depicts a sectional frontal orthogonal view of a cannulated implant having a branched distal end and side branches disposed within a cannulated bone screw with an open distal end and side port configuration.

FIG. 6 depicts a sectional orthographic frontal view of a device 40 comprising a cannulated bone screw 41 in which a cannulated implant 45 is completely inserted. The implant flange 47 disposed at the proximal end of the implant 45 retains the implant 45 within the screw 41 and thereby couples the implant 45 to the screw 41. In this embodiment the expandable distal end 49 of the implant 45 has a branched structure shown in FIG. 6 in an expanded state and branched appendages 48 along the implant longitudinal axis are disposed through side ports 43 and 44 positioned along the screw longitudinal axis. The lumen 46 of the cannulated implant is clearly shown and threaded screw cap 42 is also shown.

Figure 7:
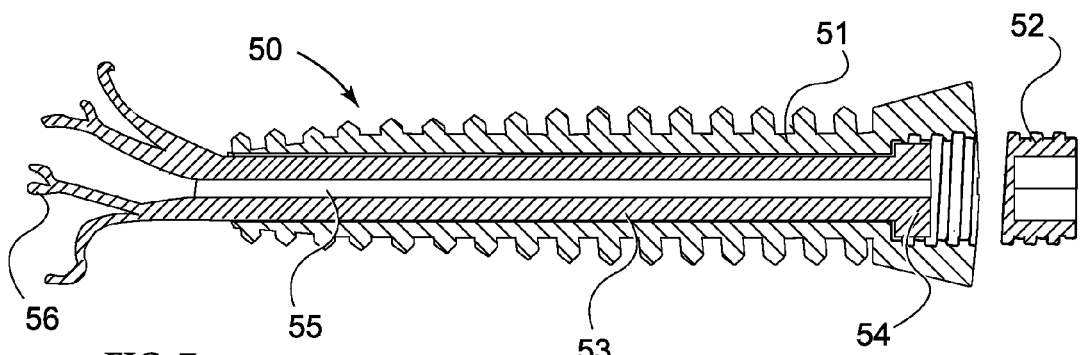
FIG. 7 depicts a sectional frontal orthogonal view of a cannulated implant having a branched distal end disposed within a cannulated bone screw with an open distal end.

FIG. 7 depicts a sectional orthographic frontal view of a device 50 comprising a cannulated bone screw 51 in which a cannulated implant 53 is completely inserted. The implant flange 54 disposed at the proximal end of the implant 53 retains the implant 53 within the screw 51 and thereby couples the implant 53 to the screw 51. In this embodiment the expandable distal end 56 of the implant 53 shown here in an expanded state comprises branches. The lumen 55 of the cannulated implant is clearly shown and threaded screw cap 52 is also shown.

Figure 8:
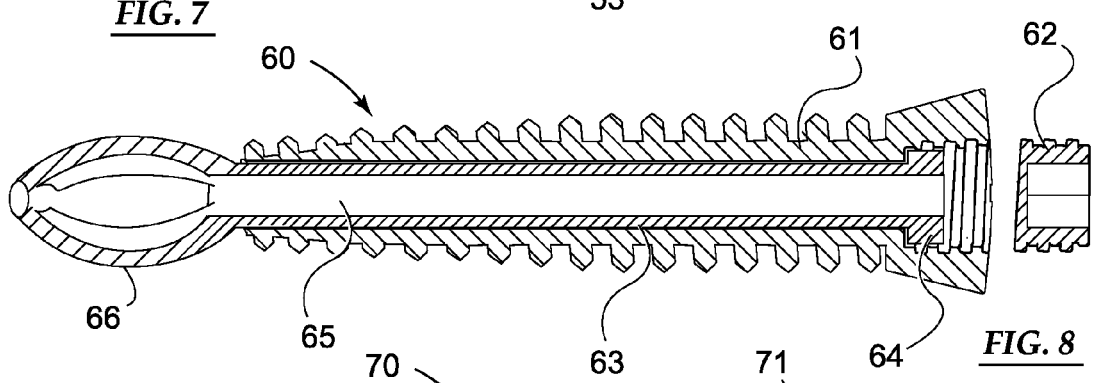
FIG. 8 depicts a sectional frontal orthogonal view of a cannulated implant having a basket-like distal end configuration disposed within a cannulated bone screw with an open distal end.

FIG. 8 depicts a sectional orthographic frontal view of a device 60 comprising a cannulated bone screw 61 in which a cannulated implant 63 is completely inserted. The implant flange 64 disposed at the proximal end of the implant 63 retains the implant 63 and thereby couples the implant 63 to the screw 61. In this embodiment the expandable distal end 66 of the implant 63 comprises a cage-like structure shown here in an expanded state. The lumen 65 of the cannulated implant is clearly shown and threaded screw cap 62 is also shown.

Figure 9:
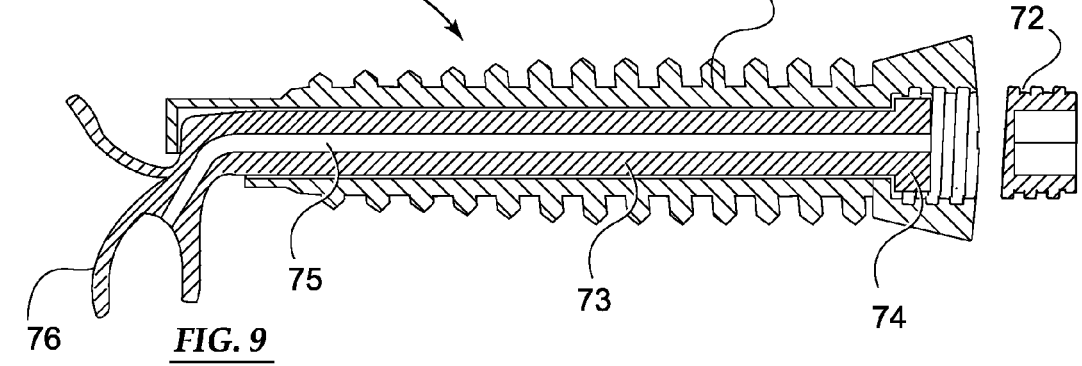
FIG. 9 depicts a sectional frontal orthogonal view of a cannulated implant having a branched distal end disposed within a cannulated bone screw with a partially open distal end.

In FIG. 9 is presented a sectional orthographic frontal view of device a 70 comprising a cannulated bone screw 71 in which a cannulated implant 73 is completely inserted. The implant flange 74 disposed at the proximal end of the implant 73 retains the implant 73 and thereby couples the implant 73 to the screw 71. In this embodiment the expandable distal end of the implant 73 comprises branches 76 shown here in an expanded state. In this embodiment the distal end of the cannulated screw 71 is configured to effect the placement of the distal end of the implant to a position about 45 degrees from the longitudinal axis of the screw 71. The lumen 75 of the cannulated implant is clearly shown and threaded screw cap 72 is also shown.

Figure 10:
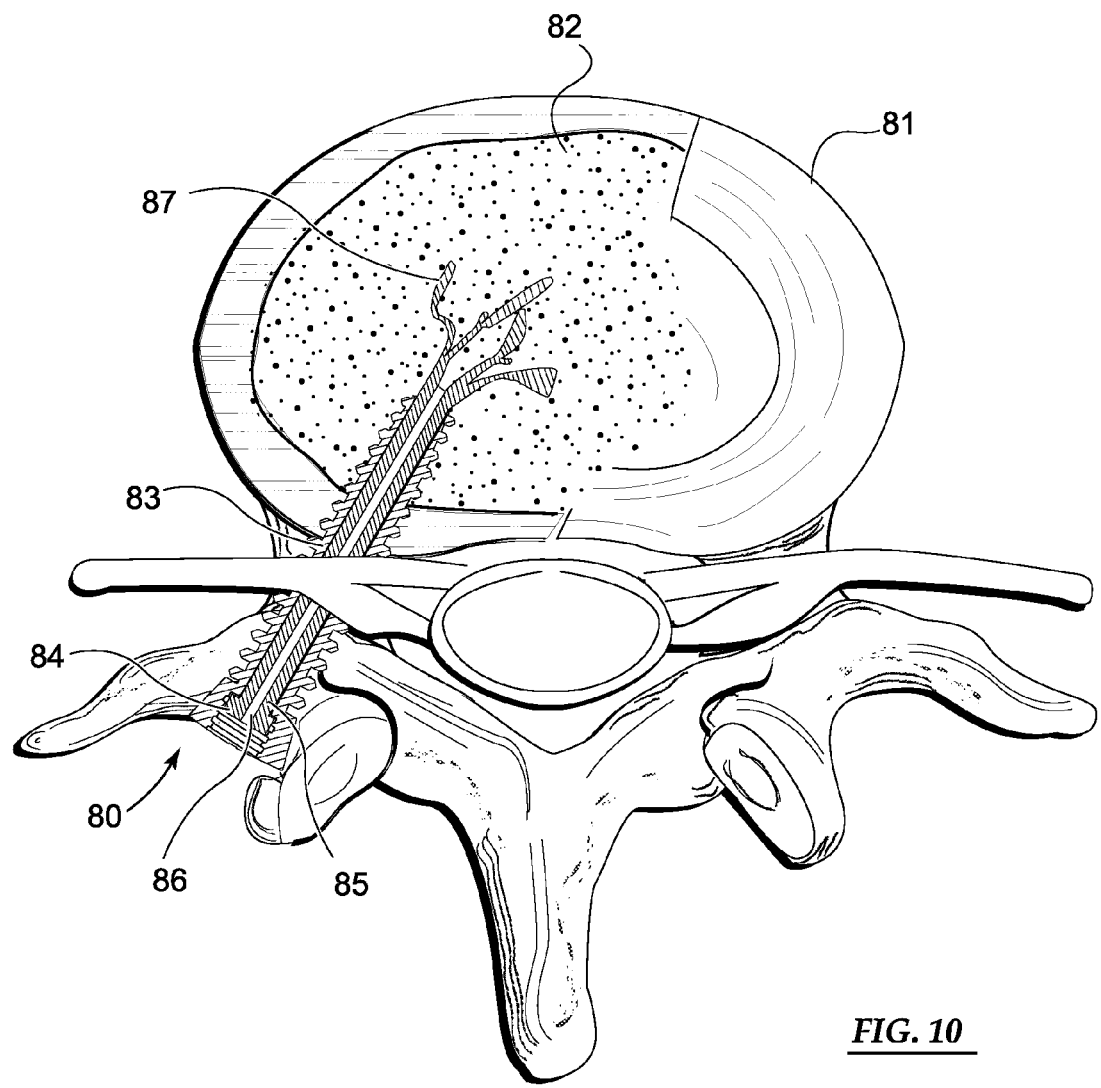
FIG. 10 depicts a partially sectional isometric view of an embodiment of a fracture fixation device deployed within a vertebral bone cavity.

In FIG. 10 is presented a sectional isometric view of a device 80 deployed in a spinal vertebra 81 wherein the cannulated screw 83 cannulated implant 85 is inserted through the wall of vertebra 81 such that the distal end of the cannulated screw 83 is disposed within the vertebral cavity 82. The cannulated implant 85 has been fully inserted into the cannulated screw 83 so that the expandable branched distal end 87 of the cannulated implant 85 is disposed within the vertebral cavity 82 and is in an expanded state. The implant flange 84 disposed at the proximal end of the implant 85 retains the implant 85 and effectively couples the implant 85 to the screw 83. The device 80 as illustrated is positioned for the delivery of a flowable composition such as bone cement through the implant lumen 86 and into the vertebral cavity 82.

Figure 11:
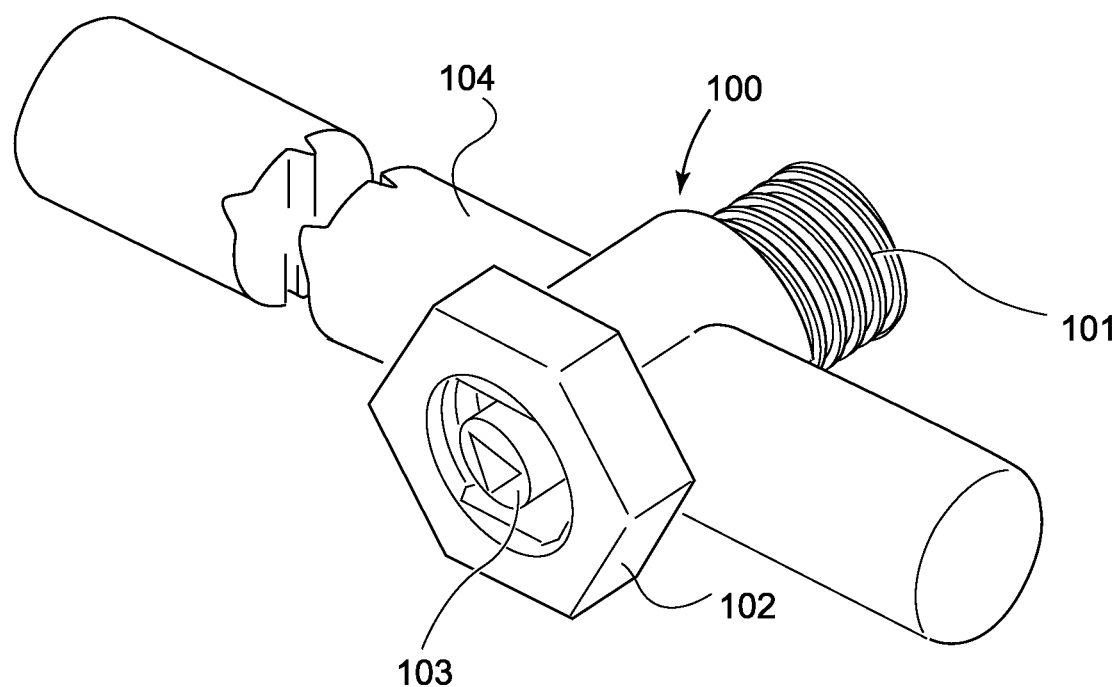
FIG. 11 depicts a sealing cap of a cannulated bone screw with an integrated coupling element for attaching orthopedic rods.

In certain embodiments of the present invention the sealing cap of the cannulated bone screw comprises an integrated coupling element that allow bone components such as spinal vertebrae to be coupled with a variety of standard orthopedic device components such as rods, pins and the like to form a fixation system. Suitable spinal fixation systems include, but are in no way limited to, systems such as those described US Patent Application 2005/027793 as well as references cited therein. In FIG. 11 is illustrated such an embodiments wherein an externally threaded cannulated bone screw sealing cap 100 with an external thread 101 and a hexagonal head 102 has an integral rod coupling element 103 that is shown coupled to a rod 104 as part of an orthopedic support or fixation system. The orthopedic screw sealing caps of the present invention can be easily modified to accommodate the wide variety of orthopedic fixation and support devices commercially available.

Figure 12A:
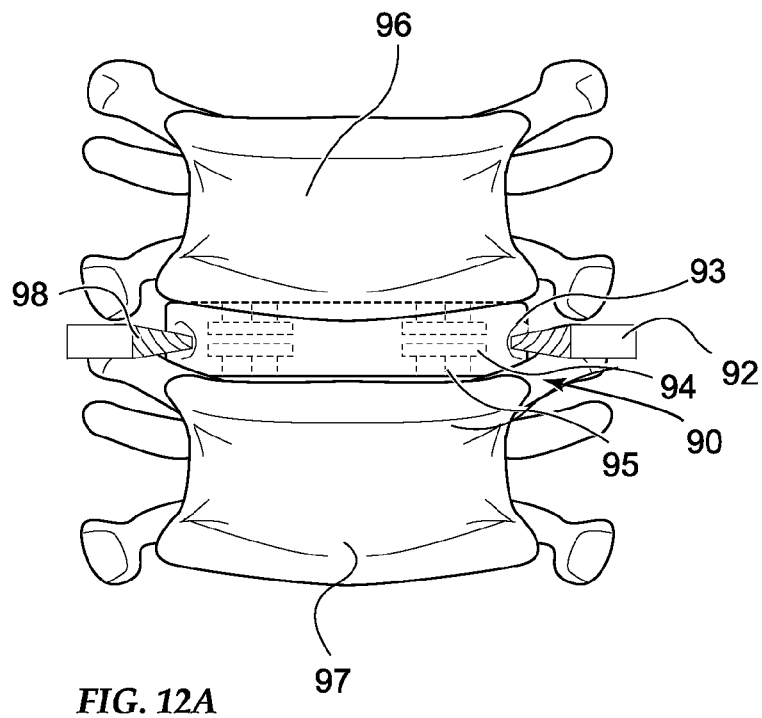
FIG. 12A depicts a disc replacement device disposed between adjacent spinal vertebrae.
Figure 12B:
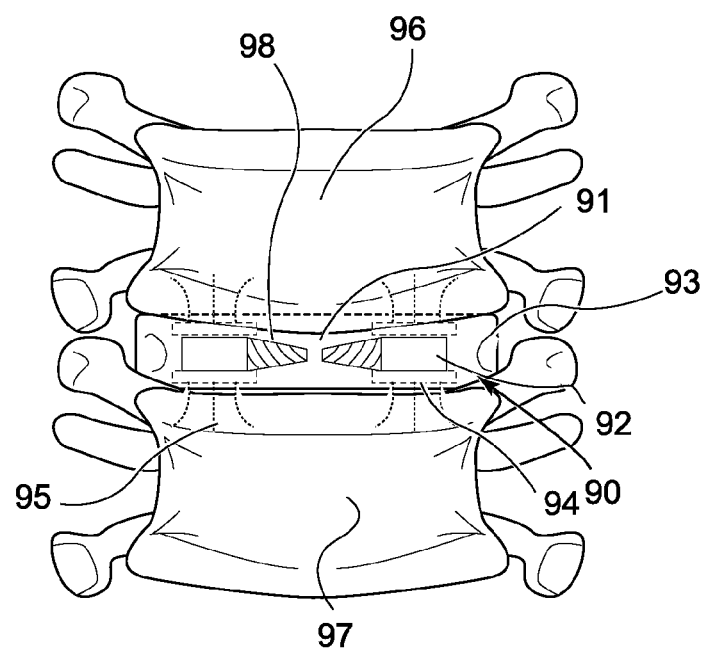
FIG. 12B depicts a disc replacement device disposed between adjacent spinal vertebrae and attached to the vertebrae.

Embodiments of expandable implant components of the present invention are useful in devices for interbody disc replacement and fusion. For example, FIGS. 12A and 12B depict a frontal view of an embodiment of a spinal disc replacement and fusion device 90 disposed between adjacent spinal vertebrae 96 and 97 wherein the fusion device 90 comprises a hollow disc-shaped body 91 having diametrically opposed access ports 93 (for simplicity only one port is numbered). Disposed within the hollow disc-shaped body 91 are four identical plates 94 (for simplicity only one plate is numbered) wherein two of the four plates 94 are arranged with the faces diametrically opposed and wherein the two pairs of four plates 94 are arranged to be laterally diametrically opposed to be accessible through access ports 93. Attached to the vertebrae-facing surfaces of each of the four plates 94 are proximal ends of a plurality of wire-like attachment members 95 such that the distal ends of a plurality of wire-like attachment members 95 can exit the hollow disc-shaped body 91 through suitably place holes in the hollow disc-shaped body 91 when the two of the four plates 94 with the faces diametrically opposed are separated. Suitable sized expander elements 92 are configured with a wedge-shaped end 98 such that when the expander elements 92 are inserted into the access ports 93 the plates 94 separate causing the wire-like attachment members 95 to exit the hollow disc-shaped body 91 and penetrate the adjacent spinal vertebrae 96 and 97 to form a fixed attachment. This series of events is clearly illustrated in FIG. 12A and FIG. 12B. Such devices can effectively function for interbody disc fusion and procedures utilizing such devices can be performed percutaneously.

In preferred embodiments of such a spinal disc fusion/replacement system the hollow disc-shaped body, the expander elements and the plates can be fabricated from a variety of material including biocompatible metals such as stainless steel and titanium or from a suitably rigid biocompatible plastic. In certain preferred embodiments the hollow disc-shaped body and/or the plates and/or the expander elements are fabricated from a poly(etheretherketone) composition also referred to as a PEEK composition. In preferred embodiments the attachment members are fabricated from a shape memory alloy such as nitinol. The description of a spinal disc replacement of the present invention illustrated in FIG. 12A and FIG. 12B and described above is exemplary with respect to the shapes, types, or particular configurations of the various elements of the illustrated devices. However, those with skill in the art will recognized that such a device configuration for performing interbody disc fusion function is not limiting and that many other configurations can be utilized depending upon the size and geometry of the implant and the implant site.

In preferred embodiments the expandable cannulated implant components of the present invention are fabricated from a variety biocompatible elastomeric materials. Examples of suitable materials include shape memory alloys (SMAs), superelastic SMAs, nitinol, MP35, Elgiloy®, spring steel and various elastomeric plastic materials or other material suitable for such implantation. For simplicity and clarity, many of the embodiments described herein are discussed as being made from a SMA, particularly nitinol, but it is understood that the benefits and features of the present invention are not limited to an SMA or nitinol, and can be achieved by using any of other suitable materials.

SMAs are materials that have the ability to return to a predetermined shape. The return is the result of a change of phase or structure that can be triggered by an external stimulus such as temperature change or electrical current. For example, when one type of SMA is below transformation temperature, it has low yield strength and can be deformed into a new shape that it will retain while it is below its transformation temperature. However, when the material is heated above its transformation temperature, it undergoes a change in crystal structure that causes it to return to its original shape. If the SMA encounters any resistance during this transformation, it can generate extremely large forces. Thus, SMAs provide a good mechanism for remote actuation. One preferred shape memory material is an alloy of nickel and titanium called nitinol. Nitinol has desirable electrical and mechanical properties, a long fatigue life, high corrosion resistance, and has similar properties to residual annular tissue and cartilaginous tissues. Other SMAs can comprise, for example, alloys of copper, zinc and aluminum or copper, aluminum and nickel. For the present invention, SMA materials or a hybrid with SMA materials can be used to make implants to reconstruct the annular and/or nuclear defects after human discectomy surgery, as well as a variety of bone fractures experienced throughout the human body.

Other types of shape memory alloys are designated as superelastic SMAs and such materials can be compressed into a small shape and upon release automatically expand to a predetermined shape. Thus, no external activation, such as temperature or electrical stimulation, is required. One preferred superelastic SMA is superelastic nitinol, which has similar properties to the SMA nitinol discussed above, but because it is a superelastic SMA does not require activation. The superelastic nitinol, or other suitable superelastic SMA, can be compressed into a small package, placed into a surgical deficit such as an annular or nuclear defect or bone fracture and, upon release, expand to a predetermined shape to fill the deficit.

In certain embodiments the expandable mechanical implant can be held in a compressed position with a sleeve fabricated from a material that is formulated to be solubilized or biodegraded rapidly upon implantation in a mammalian body. In such embodiments the combination sleeve and compressed mechanical implant is introduced through the cannulated bone screw component, wherein the sleeve dissolves or disintegrates upon exposure to body fluids and the compressed mechanical implant is allowed to expand and assume the intended final configuration. In other embodiments the sleeve is formulated to rapidly dissolve by reaction with components of bone cement. In such embodiments the combination sleeve and compressed mechanical implant is introduced through the cannulated bone screw component followed by the introduction of a suitable formulated bone cement, wherein the sleeve dissolves or disintegrates upon exposure to the bone cement and the compressed mechanical implant is allowed to expand and assume the intended final configuration.

In certain embodiments the cannula implant components have a connecting means on the proximal end with which the cannulated implant can be attached to a suitable dispensing device for the introduction of flowable material through the cannulated implant lumen and into a bone cavity. Such connecting means include, but are not limited to, standard luer fittings, luer locks, screw threads, custom fittings, adaptors and the like. Suitable dispensing means for the introduction of flowable materials through the cannulated implant lumen include, but are not limited to, syringes, piston pumps, threaded cylinders, gear driven mechanisms, hand-held guns, mechanical pumps and the like.

The sizes, configurations and shapes of specific embodiments of the components of the devices described herein will be determined by factors such as the specific medical procedure for with the device will be used, location and size of the intraosseous cavity, properties such as set-time and viscosity of the bone cement used in the procedure, and quantity of flowable material to be delivered.

In a standard unilateral vertebroplasty, the bone cement is introduced into the vertebral cavity through a single entry site commonly in or near a vertebral pedicle. The vertebral pedicle is a dense stem-like structure that projects from the posterior of a spinal vertebra. There are two pedicles per vertebra and they are contralaterally disposed with respect to the spinal chord. In a typical unilateral procedure the bone-penetrating needle or trocar is advanced under fluoroscopic guidance into a vertebral body at single site using either a transpedicular approach, wherein penetration is made through a vertebral pedicle or using a parapedicular approach, wherein penetration is made just adjacent to a vertebral pedicle. Subsequently a suitable bone cement composition is introduced through the access opening thus formed to fill the intertrabecular vertebral cavity.

Flowable materials which are dispensable with devices of the present invention include, but are not limited to, bone cement compositions, gel-like space fillers, drug carriers, polymerizable monomers, polymerizable oligomers and the like. Particularly applicable are the bone cement compositions used in vertebroplasty procedures comprising polymerizable methyl methacrylate monomers and oligomers (PMMA), which are commonly compounded with radiopacifiers such as barium salts. Typical acrylic (PMMA) bone cements useful in the present invention are available as Simplex™, from Howmedica, Rutherford, N.J.; and PALACOS™ low viscosity or OSTEOPAL V™, both available from Biomet Merck, Sjobo Sweden.

Other medically useful flowable compositions deliverable with devices of the present invention include flowable compositions comprising restorative components such as powdered corticocancellous bone or other such ground bone powder; bioactive ceramics or bioactive glasses; non-degradable or degradable hydroxyapatite; osteogenic pastes or chondrogenic pastes; bio-absorbable osteogenic compounds; carrier associated growth factors; carrier associated mineralized particles; morsellized skin or other tissue; fibrin powder or fibrin/plasminogen glue; demineralized bone matrix in carrier; poly (amino acids) and proteins as well as mixtures of one or more of these components.

Also in accordance with the present invention, there is provided a method for the dispensing of a flowable biomaterial composition into bone cavities that exist in, or that can be formed or created in, bones found anywhere in the axial and peripheral skeleton of a mammalian body. Other examples of bones which may treated in accord with the teachings herein include, but are not limited to, the clavicle, femur, humerus, hip, and scapula. More particularly the invention provides methods for injecting flowable composition such as bone cement to an interior region of a vertebral body.

We claim:

1. An orthopedic fixation device comprising:
an integrated implant system comprising;
a cannulated orthopedic screw comprising a through-bore along the longitudinal axis that defines an orthopedic screw lumen extending between an open orthopedic screw proximal end and an open orthopedic screw distal end;
a cannulated implant sized and configured to be slidably disposable within the through-bore of the orthopedic screw wherein the cannulated implant distal end comprises an expandable region that is disposed beyond the orthopedic screw distal end when the cannulated implant proximal end is disposed completely within the orthopedic screw through-bore and wherein the expandable region of the cannulated implant can be expanded to assume a predetermined configuration when disposed within a targeted location in a mammalian body; and
a screw cap attachable to the orthopedic screw proximal end that functions to seal the orthopedic screw proximal end and to fix the cannulated implant to the orthopedic screw.

2. The orthopedic fixation device of claim 1 wherein the predetermined configuration of the cannulated implant is a branched structure.

3. The orthopedic fixation device of claim 1 wherein the predetermined configuration of the cannulated implant is a cage-like structure.

4. The orthopedic fixation device of claim 1 wherein the cannulated orthopedic screw comprises one or more side ports positioned along the screw longitudinal axis and wherein the cannulated implant has branched appendages along the implant longitudinal axis wherein the appendages are disposable through the side ports.

5. The orthopedic fixation device of claim 1 wherein the cannulated implant is fabricated from a shape memory alloy.

6. The orthopedic fixation device of claim 5 wherein the shape memory alloy is nitinol.

7. The orthopedic fixation device of claim 1 wherein the lumen at the orthopedic screw proximal end is threaded and the outer surface of the screw cap is threaded such that the screw cap is threadably fixable within the proximal end of the screw.

8. The orthopedic fixation device of claim 1 wherein the screw cap further comprises one or more elements of a spinal fixation system.

9. The orthopedic fixation device of claim 1 wherein the proximal end of the cannulated implant comprises a connecting means attachable to a dispensing device for the introduction of flowable material.

10. The orthopedic fixation device of claim 1 wherein the screw is fabricated from titanium.

11. The orthopedic fixation device of claim 1 wherein the open orthopedic screw distal end is configured to effect the placement of the expanded implant.

12. A method for fracture fixation of a spinal vertebra comprising the steps of:
  i. providing a device of claim 1;
  ii. installing the cannulated orthopedic screw through a vertebral wall such that distal portion of the orthopedic screw extends into a vertebral cavity;
  iii. inserting the cannulated implant within the throughbore of the orthopedic screw such that the expandable region of the cannulated implant is disposed beyond the cannulated orthopedic screw distal end wherein the expandable region of the cannulated implant is caused or allowed to expand;
  iv. dispensing a flowable composition though the cannulated implant into the vertebral cavity; and
  v. affixing the screw cap to the orthopedic screw proximal end to effect a seal.

13. The method of claim 12 wherein the flowable composition comprises bone cement.

* * * * *